United States Patent [19]

Miller et al.

[11] 4,079,146

[45] Mar. 14, 1978

[54] METAL SALTS OF MIXED DITHIOCARBAMIC ACIDS

[75] Inventors: George Allen Miller, Glenside; Harold Edwin Carley, Chalfont; Hak-Foon Chan, Doylestown, all of Pa.

[73] Assignee: Rohm and Haas Company, Philadelphia, Pa.

[21] Appl. No.: 616,989

[22] Filed: Sep. 26, 1975

Related U.S. Application Data

[63] Continuation-in-part of Ser. No. 527,794, Nov. 27, 1974, abandoned.

[51] Int. Cl.$^2$ .............................................. C01B 6/13
[52] U.S. Cl. ............................. 424/286; 260/429 R; 260/429 K; 260/429.9; 260/435 R; 260/438.1; 260/438.5 R; 260/439 R; 260/448 R; 260/513.5; 260/534 B
[58] Field of Search ............... 260/429 K, 429 R, 534, 260/448 R, 435 R, 438.1, 429.9, 438.5, 439 R, 513.5; 424/286

[56] References Cited

U.S. PATENT DOCUMENTS

| | | | |
|---|---|---|---|
| 3,297,733 | 1/1967 | Kornicker | 260/429 R |
| 3,346,605 | 10/1967 | Windel et al. | 260/429 K |
| 3,401,182 | 9/1968 | Harvey et al. | 260/429 R |
| 3,412,117 | 11/1968 | Gagliardini | 260/429 K |
| 3,441,581 | 4/1969 | Windel et al. | 260/429 K |
| 3,517,040 | 6/1970 | Lewis et al. | 260/429 K |
| 3,725,443 | 4/1973 | Horiie et al. | 260/429 K |

FOREIGN PATENT DOCUMENTS 1,235,287   3/1967   Germany.

OTHER PUBLICATIONS

Chemical Abstracts, 65, 7068d (1966).

*Primary Examiner*—Helen M. S. Sneed
*Attorney, Agent, or Firm*—Bernard J. Burns; George W. F. Simmons; William E. Lambert, III

[57] ABSTRACT

This invention is concerned with metal salts of mixed dithiocarbamic acids, the process for their preparation and their biological activity. In particular, these salts are useful as broad spectrum fungicidal agents.

13 Claims, No Drawings

METAL SALTS OF MIXED DITHIOCARBAMIC ACIDS

SUMMARY OF THE INVENTION

This application is a continuation-in-part of copending U.S. Ser. No. 527,794, filed Nov. 27, 1974 now abandoned.

This invention relates to metal salts of mixed dithiocarbamic acids and their use as broad spectrum fungicidal agents. In particular these metal salts of mixed dithiocarbamic acids are effective in controlling *Botrytis cinerea*. This is particularly significant since alkylene-bis-dithiocarbamates are ineffective against *Botrytis cinerea*.

The metal salts of mixed dithiocarbamic acids of this invention are prepared by the following process. Aqueous or alcoholic solutions of the soluble alkali metal or ammonium salts of the following compounds are prepared:

(1) An alkylene-bis-dithiocarbamate of the general formula $$A\left(\!-\!NHC\overset{S}{\overset{\|}{\vphantom{S}}}S^-\right)_2 \quad (I)$$

wherein A is a phenylene group or an alkylene chain of 2 to 6 carbon atoms which may be branched or straight chained.

(2) An alkyl or dialkyldithiocarbamate of the formula $$(R)_2 NC\overset{S}{\overset{\|}{\vphantom{S}}} S^- \quad (II)$$

wherein R is independently selected from the group consisting of hydrogen and lower alkyl of from 1 to 4 carbon atoms.

(3) An amine of the general formula $$R^1\!-\!\overset{\overset{R^2}{|}}{N}\!-\!R^3 \quad (III)$$

or an ammonium or phosphonium salt the cation of which has the general formula $$R^1\!-\!\overset{\overset{R^2}{|}}{\underset{\underset{R^4}{|}}{N}}\!-\!R^3 \quad \text{or} \quad R^1\!-\!\overset{\overset{R^2}{|}}{\underset{\underset{R^4}{|}}{P}}\!-\!R^3$$

$$(IV) \qquad\qquad (V)$$

wherein $R^1$, $R^2$, $R^3$ and $R^4$ are independently selected from the group consisting of hydrogen, ($C_1$-$C_{20}$) alkyl, ($C_6$-$C_{10}$) aryl, ($C_7$-$C_{12}$) aralkyl, ($C_1$-$C_{20}$) hydroxyalkyl and ($C_1$-$C_{20}$) haloalkyl and $R^1$ and $R^2$ can be taken together to form a cyclic or heterogroup of the formula:

$$Z\!\!\begin{array}{c}\diagup(CH_2)_n\diagdown\\ \diagdown(CH_2)_m\diagup\end{array}\!\!N\!-\!R^3 \quad \text{or} \quad Z\!\!\begin{array}{c}\diagup(CH_2)_n\diagdown\\ \diagdown(CH_2)_m\diagup\end{array}\!\!\overset{\diagup R^3}{\underset{\diagdown R^4}{N}}$$

wherein Z can be a methylene group, an oxygen atom or a nitrogen atom and n and m can be independently an integer from 1 to 4. These solutions are mixed together in the following molar ratios:

(1) 1.0 mole of Formula (I) to
(2) about 0.1 to 10 moles of Formula (II) to
(3) about 0.1 to 6 moles of Formula (III), (IV) or (V).

To this vigorously stirred solution is added dropwise at from about 20° C. to about 80° C. an aqueous or alcoholic solution of from about 0.75 to about 6 moles of a polyvalent metal salt. A preferred molar ratio of this invention is 1.0 mole of Formula (I): to about 2.0 mole of Formula (II): to about 4.0 mole of Formula (III), (IV), or (V): and about 2.0 mole of a polyvalent metal salt. The solvents that can be utilized in this invention include water, methanol, ethanol, propanol, propylene glycol and the like, preferably water. The solutions of the reagents used in this invention are preferably at or near their saturation point but any concentration may be utilized.

The term "alkyl" as employed in the preceding preparation of the metal salts of this invention is intended to indicate an alkyl group of from 1 to 20 carbon atoms preferably from $C_1$ to $C_{10}$ which may be branched, straight chained or cyclized. The term "aryl" as employed in the preceding preparation of the metal salts of this invention is intended to indicate a phenyl or naphthyl group or a substituted phenyl or naphthyl group which may be substituted with from one to three substituents selected from the group consisting of methyl, ethyl, methoxy, ethoxy, fluoro, chloro, bromo, iodo, nitro, trihalomethyl and the like. The term "aralkyl" as employed in the preceding preparation of the metal salts of this invention is intended to indicate a benzyl group or a phenethyl group or a substituted benzyl or phenethyl group which may be substituted with from one to three substituents selected from the group consisting of methyl, ethyl, methoxy, ethoxy, fluoro, chloro, bromo, iodo, nitro, trihalomethyl and the like. The term "hydroxyalkyl" as employed in the preceding preparation of the metal salts of this invention is intended to indicate a hydroxyalkyl group of from 1 to 20 carbon atoms preferably from $C_1$ to $C_{10}$ which may be branched, straight chained or cyclized and may have up to 3 hydroxy groups. The term "haloalkyl" as employed in the preceding preparation of the metal salts of this invention is intended to indicate a haloalkyl group of from 1 to 20 carbon atoms preferably from $C_1$ to $C_{10}$ which may be branched straight chained or cyclized and may have up to 3 halo groups.

Typical compounds which are encompassed by the present invention include:

Methylammonium magnesium ethylene-bis-dithiocarbamic acid-methyldithiocarbamic acid tetraethylphosphonium calcium propylene-bis-dithiocarbamic acid-ethyldithiocarbamic acid Tripropylammonium barium butylene-bis-dithiocarbamic acid- propyldithiocarbamic acid tetra-(n-butyl)phosphonium aluminum pentylene-bis-dithiocarbamic acid-n-butyldithiocarbamic acid sec-nonylammonium lead hexylene-bis-dithiocarbamic acid-dimethyldithiocarbamic acid tetra-(4-dodecyl)phosphonium copper ethylene-bis-dithiocarbamic acid-diethyldithiocarbamic acid tri(7-eicosyl)ammonium zinc isopropylene-bis-dithiocarbamic acid-isopropyldithiocarbamic acid triphenylphosphonium cadmium sec-butylene-bis-dithiocarbamic acid-sec-butyldithiocarbamic acid di-(o,p-diethylphenyl)ammonium chromium sec-pentylene-bis-dithiocarbamic acid-dipropyldithiocarbamic acid 3,4-dihydro-1,3-oxazetidinium manganese sec-hexylene-bis-dithiocarbamic acid-di(n-butyl)dithiocarbamic acid hexahydro-1,3-oxazocinium cobalt-phenylene-bis-dithiocarbamic acid-diisobutyldithiocarbamic acid decahydroazecinium nickel phenylene-bis-dithiocarbamic acid-di(t-butyl)dithiocarbamic acid 3,5-dimethoxynaphthylammonium copper isopropylene bis-dithiocarbamic acid-dimethyldithiocarbamic acid tetra-(2,4,6-trihydroxyheptyl)ammonium manganese isobutylene-bis-dithiocarbamic acid-dimethyldithiocarbamic acid tetrachloromethylphosphonium aluminum phenylene-bis-dithiocarbamic acid-dimethyldithiocarbamic acid tetra-1-fluoroethylphosphonium chromiumphenylene-bis-dithiocarbamic acid-dimethyldithiocarbamic acid tetra-1-bromodecylphosphonium magnesium pentylene-bis-dithiocarbamic acid-dimethyldithiocarbamic acid tetra-(t-butylphenyl)phosphonium zinc hexylene-bis-dithiocarbamic acid-diethyldithiocarbamic acid tetra-(2-chloro-4-nitrophenyl)ammonium zinc propylene-bis-dithiocarbamic acid-dipropyldithiocarbamic acid tetra-(2-methoxy-3-methylphenyl)phosphonium copper ethylene-bis-dithiocarbamic acid-diethyldithiocarbamic acid tetra-(2-nitro-4-trifluoromethylphenyl)phosphonium manganese ethylene-bis-dithiocarbamic acid-dimethyldithiocarbamic acid tetra-(3-methyl-5-cyanobenzyl)phosphonium cobalt propylene-bis-dithiocarbamic acid-dipropyldithiocarbamic acid di-(3,5-dimethylphenethyl)ammonium chromium n-butylene-bis-dithiocarbamic acid-diisobutyldithiocarbamic acid tetra-(2-bromo-4-chlorophenyl)phosphonium nickel propylene-bis-dithiocarbamic acid-dimethyldithiocarbamic acid methylethylpropylammonium zinc ethylene-bis-dithiocarbamic acid-dimethyldithiocarbamic acid tetramethylphosphonium zinc ethylene-bis-dithiocarbamic acid-diethyldithiocarbamic acid di-(2,4,5-trichlorophenyl)phosphonium zinc propylene-bis-dithiocarbamic acid-diethyldithiocarbamic acid tetra-(2-chloro-3,5-dimethylphenyl)phosphonium copper ethylene-bis-dithiocarbamic acid-dipropyldithiocarbamic acid tetra-(2-methyl-3,5-dichlorophenyl)phosphonium manganese ethylene-bis-dithiocarbamic acid-dimethyldithiocarbamic acid 3,4,5-trimethoxy phenyl ammonium magnesium propylene-bis-dithiocarbamic acid-dimethyldithiocarbamic acid 2,3,4-trimethylphenyl ammonium zinc ethylene-bis-dithiocarbamic acid-dimethyldithiocarbamic acid 2,4,6-tri-t-butylphenyl ammonium zinc ethylene-bis-dithiocarbamic acid-dimethyldithiocarbamic acid It is believed that the metal salts of mixed dithiocarbamic acids prepared by this process apparently combine in the following stoichiometric ratio:

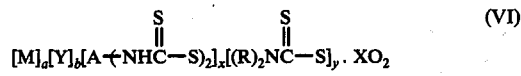

$$[M]_a[Y]_b[A(-NHC(=S)-S)_2]_x[(R)_2NC(=S)-S]_y \cdot XO_2 \quad (VI)$$

wherein A and R are as defined above; M is a metal cation selected from Groups IIA, IIIA, IVA, IB, IIB, VIB, VIIB, and VIII of the Periodic Table; Y is a group as defined by either Formula (III), (IV), or (V); $a$, $b$, $x$ and $y$ are integers and X can be zero or an integer.

When Y is a group defined by Formula (III), $a$ is an integer which is equal to $x + y/2$ and $b$ is equal to 1 or 2. When Y is a group defined by Formula (IV) or (V) $a$, $b$, $x$ and $y$ are integers which have the relationship that $2a + b$ is equal to $2x + y$.

A preferred embodiment of this invention is the metal salt of mixed dithiocarbamic acids formed by mixing aqueous solutions of one mole of an alkali metal salt of alkylene-bis-dithiocarbamate to about two moles of an alkali metal salt of alkyl or dialkyldithiocarbamate and at least about two moles preferably about four moles of a group of Formula (III), (IV), or (V) wherein $R^1$, $R^2$, $R^3$ and $R^4$ are as defined above; then adding dropwise to this mixture, at from about 25° C. to 40° C. with vigorous stirring, an aqueous solution of about two moles of a metal salt, filtering the resultant precipitate, washing it with water and drying it at 40° C. to a constant weight.

Another preferred embodiment of this invention is the metal salt of mixed dithiocarbamic acids formed by simultaneously adding aqueous solutions of (a) one mole of an alkali metal salt of alkylenebisdithiocarbamate and about two moles of an alkali metal salt of alkyl or dialkyldithiocarbamate and (b) an aqueous solution of about two moles of a metal salt to an aqueous solution of about four moles of a group of Formula (III), (IV) or (V) wherein $R^1$, $R^2$, $R^3$ and $R^4$ are as defined above, at temperatures of from about 25° C. to about 40° C. with vigorous stirring. The resultant precipitate is filtered washed with water and dried at 40° C. to a constant weight.

Another preferred embodiment of this invention is the metal salt of mixed dithiocarbamic acids formed by mixing an aqueous solution of one mole of an alkali metal salt of alkylene-bis-dithiocarbamate, about two moles of an alkali metal salt of alkyl or dialkyldithiocarbamate and about four moles of a group of Formula (III), (IV) or (V), wherein $R^1$, $R^2$, $R^3$ and $R^4$ are as defined above, simultaneously with an aqueous solution of about two moles of a metal salt, the point of mixing taking place in a vigorously stirred vessel which may or may not contain water, at temperatures of from about 25° C. to about 40° C.

In the more preferred embodiment of this invention, the metal salts which can be utilized can be selected from any of the following combinations of metal ions such as Mg, Ca, Ba, Al, Pb, Cu, Zn, Cd, Cr, Mn, Co, and Ni and any of the following anion counterions such as chloride, bromide, iodide, sulfate, bisulfate, phosphate, nitrate, perchlorate, carbonate, bicarbonate, hydrosulfide, hydroxide, acetate, oxalate, malate, nitrate or tartarate; the most preferred salt being zinc chloride.

The most preferred alkylene-bis-dithiocarbamate which can be utilized in the above procedure is ethylene-bis-dithiocarbamate and the most preferred dialkyldithiocarbamate is dimethyl dithiocarbamate.

The following examples are provided merely to facilitate one skilled in the art to better understand how to prepare exemplary complex metal salts of this invention. It is understood, however, that these examples are intended for illustration only and it is not intended that the invention be limited thereby.

EXAMPLE 23

Trimethylammonium Manganese Ethylene-bis-dithiocarbamic acid-Dimethyldithiocarbamic acid A 100 ml. aqueous solution of 8.44g. (0.05 mole) of manganese sulfate monohydrate is added dropwise to a 3-necked flask. After 5–10 ml. of the solution has been added, a combined 100 ml. aqueous solution of 6.6g. of sodium ethylene-bis-dithiocarbamate (0.025 mole), 8.95g. of sodium dimethyldithiocarbamate (0.05 mole) and 9.5g. (0.1 mole) of trimethylamine hydrochloride is added simultaneously to the flask at the same rate as that of the metal salt solution. After the addition (ca 15 min.) the suspension is stirred for 0.5 hour then vacuum filtered, reslurried with water, and filtered again. The collected precipate is air-dried overnight then vacuum dried until it reaches a constant weight. A total of 13.7g. of product, mp>250° C. (dec) is obtained.

EXAMPLE 50

Preparation of Tetramethylammonium Zinc Ethylene-bis-dithiocarbamic acid-Dimethyldithiocarbamic acid Aqueous solutions (20%) of disodium ethylene-bis-dithiocarbamate (6.85g., 0.025 mole), dimethyldithiocarbamic acid sodium salt dihydrate(9.0g., 0.05 mole), and tetramethyl ammonium bromide (15.4g., 0.1 mole) are prepared separately. The above solutions are then mixed to this mixture is added an aqueous solution (20%) of zinc chloride (6.96g., 0.05 mole) dropwise with rapid stirring. The reaction mixture is stirred for 10 more minutes. The precipitate formed is collected by filtration and washed with water. It is dried in a vacuum oven at 40° until it gives a constant weight. A total of 15.7g. of product, mp. 134°–6° C. is obtained.

EXAMPLE 51

Preparation of Ammoniated Zinc Ethylene-bis-dithiocarbamic acid-Dimethyldithiocarbamic acid Aqueous solutions (20%) of disodium ethylene-bis-dithiocarbamate (6.85g., 0.025 mole) and dimethyldithiocarbamic acid sodium salt dihydrate (9.0g., 0.05 mole) are prepared separately and then mixed together. To this mixture is added 6.75 ml. (0.1 mole) of concentrated ammonium hydroxide followed by addition dropwise of an aqueous solution (20%) of zinc chloride (6.96g., 0.05 mole) with rapid stirring. The reaction mixture is stirred for 10 more minutes. The precipitate formed is collected by filtration and washed with water. It is dried in a vacuum oven at 40° C. until it gives a constant weight. A total of 14g., of product, mp. 142°–5° C. is obtained.

EXAMPLE 52

Preparation of Dimethylammonium Zinc Ethylene-bis-dithiocarbamic acid-Dimethyldithiocarbamic acid Aqueous solutions (20%) of disodium ethylene-bis-dithiocarbamate (6.85g., 0.025 mole), dimethyldithiocarbamic acid sodium salt dihydrate (9.0g., 0.05 mole), and dimethylamine hydrochloride (8.2g., 0.1 mole) are prepared separately. To a mixture of the above solutions is added an aqueous solution (20%) of zinc chloride (6.96g., 0.05 mole) dropwise with rapid stirring. The reaction mixture is stirred for 10 more minutes. The precipitate formed is collected by filtration and washed with water. It is then dried in a vacuum oven at 40° C. until it gives a constant weight. A total of 14.2g. of product, mp. 137°–41° C. is obtained.

EXAMPLE 53

Trimethyl(2-hydroxyethyl)ammonium Zinc Ethylene-bis-dithiocarbamic acid-Dimethyldithiocarbamic acid A 100 ml. aqueous solution of 6.95g. (0.05 mole) of zinc chloride is added dropwise to a 3-necked flask containing 50 ml. of water. After 5–10 ml. of the solution has been added, a combined 100 ml. aqueous solution of 6.5g. (0.025 mole) of sodium ethylene-bis-dithiocarbamate, 8.95g. (0.05 mole) of sodium dimethyldithiocarbamate and 13.6g. (0.1 mole) of trimethyl(2-hydroxyethyl)ammonium chloride (choline chloride) is added to the flask at the same rate as that of the metal salt solution. After the addition, the suspension is stirred 0.5 hour then filtered under vacuum, reslurried with water, and filtered again. The collected precipitate is air-dried overnight then dried under vacuum until it reaches a constant weight. A total of 15.3g. of product, mp 120°–124° C. is obtained.

EXAMPLE 54

Tetramethylammonium Zinc Ethylene-bis-dithiocarbamic acid-Dimethyldithiocarbamic acid To a well stirred aqueous solution of 6.85g. (0.027 mole) of sodium ethylene-bis-dithiocarbamate, 9.0g., (0.05 mole) of sodium dimethyldithiocarbamate and 10.9g. (0.1 mole) of tetramethylammonium chloride is added dropwise at room temperature 6.96g. (0.05 mole) of zinc chloride dissolved in 30 ml. of water. A very fine dispersed white precipitate forms immediately. The reaction mixture is stirred for an additional ten minutes then filtered under vacuum. The collected solid is transferred to a beaker, reslurried with water, then filtered again. The white solid is air-dried for two days then dried under vacuum at 45° C. until it reaches a constant weight. A total of 15.2g. of products mp. 128°–132° C. is obtained.

EXAMPLE 55

Trimethylammonium Zinc Ethylene-bis-dithiocarbamic acid-Dimethyldithiocarbamic acid A 100 ml. aqueous solution of 6.95g. (0.05 mole) of zinc chloride is added dropwise to a 3-necked flask containing 50 ml. of water. After 5–10 ml. of the solution has been added, a combined 100 ml. aqueous solution of 6.5g. (0.025 mole) of sodium ethylene-bis-dithiocarbamate, 8.95g. (0.05 mole) of sodium dimethyldithiocarbamate and 9.6g. (0.1 mole) of trimethylamine hydrochloride is added to the flask at the same rate as that of the metal salt solution. After the addition, the suspension is stirred 0.5 hour then filtered under vacuum, reslurried with water and filtered again. The collected precipitate is air-dried overnight then dried under vacuum at 45° until it reaches a constant weight. A total of 14.6g. of product, mp 134°-137° C is obtained.

EXAMPLE 57

Trimethylammonium Manganese-Zinc Ethylene-bis-dithiocarbamic acid-Dimethyldithiocarbamic acid A 100 ml. aqueous solution of 8.44g. (0.05 mole) of manganese sulfate monohydrate is added dropwise to a 3-necked flask. After 5–10 ml. of the solution had been added, a combined 100 ml. solution of 6.5g. of sodium ethylene-bis-dithiocarbamate (0.025 mole), 8.95g. of sodium dimethyldithiocarbamate (0.05 mole) and 9.5g. (0.1 mole) of trimethylamine hydrochloride is added simultaneously to the flask at the same rate as that of the manganese solution. After the addition (ca 15 min.) the suspension is stirred for 0.5 hour then vacuum filtered. The precipitate is added to a beaker containing 100 ml. of water and a solution of $ZnCl_2$ (0.005 mole) is added with efficient stirring. The suspension is refiltered and the precipitate is air-dried for six hours then vacuum dried until it reaches a constant weight. A total of 14.4g. of product, mp > ~250° C. (dec.) is obtained.

EXAMPLE 75

Dimethylammonium Manganese Piperazine dithiocarbamic acid-Dodecyldithiocarbamic acid Sodium hydroxide 4.0g. (0.1 mole) is added to a 3-necked flask containing an addition funnel, a mechanical stirrer, and a reflux condenser. Water (25 ml.) is added and the solution is stirred at room temperature while 2.15g. (0.025 mole) of piperazine and 9.25g. (0.05 mole) of dodecylamine is added. Carbon disulfide 7.6g (0.1 mole) is then added at such a rate so as to keep the flask temperature below 46° C. The orange solution is stirred for 2.5 hours after which time 8.15g. (0.1 mole) of dimethylamine hydrochloride is added followed by a solution of 9.9g. (0.05 mole) of $MnCl_2.4H_2O$. The suspension is stirred an additional 0.5 hour then vacuum filtered, reslurried, and re-filtered. The collected precipitate is air-dried overnight then vacuum dried until it reaches a constant weight. A total of 20.7g. of product mp. 200° C. (dec.) is obtained.

EXAMPLE 85

Preparation of N,N-Dimethylethanolammonium Zinc Ethylene-bis dithiocarbamic acid-Dimethyldithiocarbamic acid Aqueous solutions (20%) of disodium ethylene-bis-dithiocarbamate (6.85g., 0.025 mole), dimethyldithiocarbamic acid sodium salt dihydrate (9.0g., 0.05 mole), and N,N-dimethylethanol amine (8.9g., 0.1 mole) are prepared separately. The above solutions are then mixed and to this mixture is added an aqueous solution (20%) of zinc chloride (6.96g., 0.05 mole) dropwise with rapid stirring. The reaction mixture is stirred for 10 more minutes. The precipitate formed is collected by filtration and washed with water. It is dried in a vacuum oven at 40° C. until it gives a constant weight. A total of 12.5g. of product, mp. 211°-214° C. is obtained.

EXAMPLE 86

(n-Butyl)-triphenylphosphonium Zinc Ethylene-bis-dithiocarbamic acid Dimethyldithiocarbamic acid Ten grams (0.05 mole) of (n-butyl)-triphenylphosphonium bromide is added to 100 ml. of water contained in a 3-necked flask. To this homogeneous solution is slowly added a 100 ml. aqueous solution of zinc chloride 6.8g. (0.05 mole). After about 10 ml. of the zinc chloride solution has been added, a combined 100 ml. aqueous solution of sodium dimethyldithiocarbamate 8.95g. (0.05 mole) is added at the same rate as that of the metal salt solution. At the end of the addition the voluminous precipitate that forms is collected by vacuum filtration and air-dried overnight then dried under vacuum until it reaches a constant weight. A total of 27.4g. of product mp 79°-81° C. is obtained.

EXAMPLE 87

General procedure for the preparation of trimethyl (2-hydroxyethyl) ammonium Zinc Ethylene-bis-dithiocarbamic acid-dimethyldithiocarbamic acid A 100 ml. aqueous solution of the zinc chloride is added dropwise to a 3-necked flask containing 50 ml. of water. After 5–10 ml. of the solution has been added, a combined 100 ml. aqueous solution of sodium ethylenebisdithiocarbamate, sodium dimethyldithiocarbamate and trimethyl (2-hydroxyethyl) ammonium chloride (choline chloride) is added to the flask at the same rate as that of the metal salt solution. After the addition, the suspension is stirred for 0.5 hour then filtered under vacuum reslurried with water, and filtered again. The collected precipitate is air-dried overnight then dried under vacuum until it reaches a constant weight.

Table I below gives the metal salt complexes which can be formed by the utilization of the procedures given in Examples 23, 50, 51, 52, 53, 54, 55, 58, 75, 85, 86 and 87 when the following ratios of reagents are used:

(a) one mole of disodium ethylene-bis-dithiocarbamate;
(b) two moles of sodium dimethyldithiocarbamate;
(c) two moles of zinc sulfate and;
(d) four moles of a quaternary ammonium salt.

TABLE I

| Example No. | $R^1R^2R^3R^4\overset{+}{N}X^-$ | mp° C | C | H | N | S | Zn |
|---|---|---|---|---|---|---|---|
| | | | Elemental Analysis - % Found | | | | |
| 1 | $(CH_3)_4\overset{+}{N}$ $Br^-$ | 126–9 | 24.90 | 4.37 | 10.47 | 37.12 | 13.10 |
| 2 | $(CH_3)_3N \cdot HCl$ | >250 | 22.34 | 3.84 | 10.00 | 3.30 | 17.3 |
| 3 | $CH_3NH_2 \cdot HCl$ | 141–5 | 21.24 | 3.37 | 10.762 | 41.87 | 19.1 |
| 4 | $(CH_3)_2NH \cdot HCl$ | 138–42 | 22.57 | 3.73 | 10.65 | 43.04 | 19.4 |
| 5 | $n-C_4H_9NH_2 \cdot HCl$ | 116–8 | 25.97 | 4.66 | 10.91 | 40.13 | 16.7 |

TABLE I-continued

| Example No. | $R^1R^2R^3R^4\overset{+}{N}X^-$ | mp° C | Elemental Analysis - % Found | | | | |
|---|---|---|---|---|---|---|---|
| | | | C | H | N | S | Zn |
| 6 | (cyclohexyl)NH . HCl | 125–8 | 26.32 | 4.34 | 10.41 | 44.42 | 17.9 |
| 7 | $Ph\overset{+}{N}(CH_3)_3Br^-$ | 80–5 | 32.55 | 4.60 | 10.44 | 36.23 | 14.8 |
| 8 | $(CH_3)_3\overset{+}{N}CH_2CH_2OHCl^-$ | 109–12 | 25.07 | 4.24 | 10.15 | 32.29 | 18.1 |
| 9 | $PhCH_2\overset{+}{N}(CH_3)_3I$ | 103–6 | 33.78 | 4.74 | 9.54 | 33.2 | 12.4 |
| 10 | $n\text{-}C_8H_{17}NH_2 . HCl$ | 112–6 | 33.93 | 5.84 | 10.60 | 36.42 | 13.1 |
| 11 | $NH_2(CH_2)_3NH_2 . 2HCl$ | 129–34 | 21.95 | 3.70 | 10.68 | 40.92 | 17.1 |
| 12 | $CH_3(CH_2)_{17}\overset{+}{N}(CH_3)_2CH_2PhCl^-$ | 73–8 | 51.73 | 8.19 | 6.83 | 23.25 | 9.0 |
| 13 | $NH_2CH_2CH_2NH_2 . 2HCl$ | 115–7 | 21.84 | 3.71 | 11.10 | 41.63 | 17.0 |
| 14 | (morpholine)NH . HCl | 128–32 | 24.74 | 4.02 | 10.76 | 40.17 | 16.9 |
| 15 | $CH_3(CH_2)_{11}NH_2 . HCl$ | 86–9 | 48.56 | 9.26 | 8.31 | 20.98 | 9.20 |
| 16 | $HOCH_2CH_2NH_2 . 1HCl$ | 124–7 | 21.37 | 3.51 | 10.40 | 39.62 | 18.10 |
| 17 | $NH_2(CH_2)_6NH_2 . 2HCl$ | 126–30 | 24.33 | 4.25 | 11.02 | 46.77 | 15.50 |
| 18 | $CH_3CH(NH_2)CH_2CH_3 . HCl$ | 119–23 | 23.54 | 4.06 | 9.96 | 26.66 | 16.80 |
| 19 | $CH_3(C_2)_{13}N(CH_3)_2 . HCl$ | 88–93 | 41.81 | 7.60 | 8.33 | 26.26 | 13.1 |

Table II below gives the metal salt complexes formed by the utilization of the following reagents when the procedures of Examples 23, 50, 51, 52, 53, 54, 55, 58, 75, 85, 86 and 87 are followed:
(a) one mole of disodium ethylene-bis-dithiocarbamate;
(b) two moles of sodium dimethyldithiocarbamate;
(c) two moles of manganese sulfate and;
(d) four moles of a quaternary ammonium salt.

When the procedures of Examples 23, 50, 51, 52, 53, 54, 55, 58, 75, 85, 86 and 87 are followed and the following ratios of reagents are utilized the metal salt complexes of Table III are readily obtained:
(a) one mole of disodium ethylene-bis-dithiocarbamate
(b) two moles of sodium dimethyldithiocarbamate
(c) two moles of a metal salt and,
(d) four moles of a quaternary ammonium salt.

Table II

| Example No. | $R^1R^2R^3R^4\overset{+}{N}X^-$ | mp° C. | Elemental Analysis - % Found | | | | | |
|---|---|---|---|---|---|---|---|---|
| | | | C | H | N | S | Mn | O |
| 20 | $n\text{-}C_4H_9NH_2 . HCl$ | 230 (dec.) | 22.83 | 3.80 | 9.43 | 39.33 | 16.2 | 9.47 |
| 21 | $N\text{-}C_8H_{17}NH_2 . HCl$ | 229–31 | 35.96 | 6.34 | 9.44 | 30.60 | 7.00 | 9.96 |
| 22 | $PhCH_2\overset{+}{N}(CH_3)_3I^-$ | >50 | 31.82 | 4.54 | 8.86 | 27.44 | 9.80 | 9.00 |
| 23 | $(CH_3)_3N . HCl$ | >250 | 21.71 | 3.60 | 9.90 | 49.89 | 15.30 | 7.89 |
| 24 | (cyclohexyl)NH . HCl | 250 (dec.) | 25.44 | 4.10 | 10.19 | 38.33 | 13.40 | 9.13 |
| 25 | $(CH_3)_2NH . HCl$ | >250 | 21.38 | 3.38 | 11.25 | 38.71 | 16.3 | 10.1+ |
| 26 | $HOCH_2CH_2NH_2 . HCl$ | >250 | 20.04 | 3.25 | 9.32 | 40.63 | 16.0 | 12.61 |
| 27 | $NH_2CH_2CH_2NH_2 . 2HCl$ | >250 | 20.21 | 3.35 | 10.25 | 36.88 | 14.3 | 13.33 |
| 28 | $NH_2(C_2)_6NH_2 . 2HCl$ | >250 | 22.54 | 3.80 | 1.26 | 37.28 | 13.8 | 12.89 |
| 29 | (morpholine)NH . HCl | >250 | 21.36 | 3.56 | 9.94 | 36.62 | 14.2 | 12.56 |
| 30 | $HC\equiv CC(CH_3)_2NH_2 . HCl$ | >250 | 21.24 | 3.36 | 9.79 | 21.20 | 15.2 | 11.6+ |
| 31 | $(CH_3)_2\overset{+}{N}CH_2CH_2OHCl^-$ | >250 | 22.81 | 3.70 | 9.24 | 32.59 | 15.2 | 9.88 |
| 32 | $CH_3CH(NH_2)CH_2CH_3 . HCl$ | >250/ 250 | 21.86/ 12.12 | 3.73 | 9.27 | 35.37/ 10.15 | | |
| 33 | $(CH_3)_3CCH_2C(CH_3)_2NH_2 . HCl$ | | 25.78 | 4.53 | 9.85 | 34.95 | 12.3 | 8.17 |
| 34 | $(HOCH_2CH_2)_3N . HCl$ | >250 | 23.80 | 3.60 | 10.24 | 38.44 | 15.2 | 6.02 |
| 35 | $PhCH_2NH_2 . HCl$ | 230 (dec.) | 2.68 | 3.79 | 1.57 | 35.10 | 13.0 | 5.50 |
| 36 | $NH_4OH$ | 235 | 19.13 | 3.15 | 8.44 | 33.56 | 19.1 | 12.05 |
| 37 | t-$C_8$ amines (mixture) | 240 (dec.) | 39.00 | 6.63 | 7.17 | 25.43 | 9.2 | 10.++ |
| 38 | $CH_3(CH_2)_{17}\overset{+}{N}(CH_3)_2CH_2PhCl^-$ | 115 | 48.98 | 7.60 | 6.52 | 18.70 | 6.4 | 6.77 |
| 39 | $CH_3(CH_2)_{11}NHC(NH)NH_2 . CH_3COOH$ | 205 (dec.) | 31.99 | 5.60 | 9.94 | 19.38 | 6.2 | 8.67 |

Table III

| Example No. | Metal Salt | $R^1R^2R^3R^4N^+X^-$ | mp° C | Elemental Analysis - % Found | | | | | |
|---|---|---|---|---|---|---|---|---|---|
| | | | | C | H | N | S | Metal | O |
| 40 | $MnCl_2$ | $(CH_3)_4N^+Br^-$ | 250 (dec) | 23.18 | 3.98 | 9.74 | 38.50 | 13.7/— | — |
| 41 | $NiCl_2 . 6H_2O$ | $(CH_3)_3N . HCl$ | >250 | 21.45 | 3.43 | 10.88 | 37.05 | 17.5/— | — |
| 42 | $FeCl_3 . 6H_2O$ | $(CH_3)_3N . HCl$ | 228–32 | 21.92 | 3.35 | 10.88 | 36.85 | 11.40/— | 5.28 |

Table III-continued

| Example No. | Metal Salt | $R^1R^2R^3R^4N^+X^-$ | mp° C | C | H | N | S | Metal | O |
|---|---|---|---|---|---|---|---|---|---|
| 43 | $CoCl_2$ | $(CH_3)_3N \cdot HCl$ | >250 | 21.32 | 3.29 | 9.58 | 35.88 | 13.70/— | 6.09 |
| 44 | $CdCl_2$ | $(CH_3)_3N \cdot HCl$ | >250 | 18.79 | 3.06 | 8.51 | 33.94 | 29.0/— | 3.29 |
| 45 | $CuBr_2$ | $(CH_3)_3N \cdot HCl$ | >250 | 19.86 | 3.27 | 9.40 | 30.42 | 19.3/— | 3.24 |
| 46 | $MnCl_2$ | $(CH_3)_3N \cdot HCl$ | >250 | 25.26 | 4.59 | 11.28 | 40.68 | 13.40/— | 3.90 |
| 47 | $CuSO_4$ | $(CH_3)_3NCH_2CH_2OHCl^-$ | >250 | 22.27 | 4.45 | 9.92 | 35.78 | 18.3/— | 5.12 |
| 48 | $FeCl_3 \cdot 6H_2O$ | $CH_3NH_2 \cdot HCl$ | 205–210 | 22.25 | 3.22 | 10.76 | 44.88 | 11.1/— | 5.83 |
| 49 | $FeCl_3 \cdot 6H_2O$ | $(CH_3)_3N^+CH_2CH_2OHCl^-$ | 200 | 24.17 | 3.54 | 11.4 | 42.12 | 11.4/— | 7.68 |
| 50 | $ZnCl_2$ | $(CH_3)_4N^+Br^-$ | 134–6 | 24.70 | 4.56 | 10.40 | 39.43 | 17.80/— | — |
| 51 | $ZnCl_2$ | $N^+H_4OH^-$ | 142–5 | 19.18 | 4.04 | 13.81 | 41.41 | 18.10/— | — |
| 52 | $ZnCl_2$ | $(CH_3)_2N \cdot HCl$ | 137–41 | 21.70 | 3.64 | 10.43 | 40.12 | 16.50/— | — |
| 53 | $ZnCl_2$ | $(CH_3)_3N^+CH_2CH_2OHCl^-$ | 120–4 | 25.60 | 4.51 | 10.49 | 38.14 | 16.80/— | 8.06 |
| 54 | $ZnCl_2$ | $(CH_3)_4N^+Cl^-$ | 128–32 | 24.56 | 4.28 | 10.61 | 39.55 | 17.20/— | — |
| 55 | $ZnCl_2$ | $(CH_3)_3N \cdot HCl$ | 134–37 | 22.64 | 3.83 | 10.58 | 38.43 | 18.5/— | — |
| 56 | $CuSO_4$ | $(CH_3)_3N \cdot HCl$ | 220 (dec) | 21.54 | 3.39 | 9.89 | 38.19 | 21.2/— | 3.13 |
| 57 | $MnSO_4 \cdot H_2O/ZnCl_2$ | $(CH_3)_3N \cdot HCl$ | 250 (dec) | 22.95 | 3.95 | 10.57 | 40.36 | 14.1/0.5 | 6.08 |
| 58 | $ZnCl_2/FeCl_3 \cdot 6H_2O$ | $CH_3NH_2 \cdot HCl$ | 140–5 | 20.73 | 3.21 | 10.39 | 42.53 | 18.6/0.5 | 3.47 |
| 59 | $MnSO_4 \cdot H_2O/CuSO_4$ | $CH_3NH_2 \cdot HCl$ | >250 | 18.33 | 3.18 | 8.85 | 34.93 | 13.8/2.9 | 14.05 |
| 60 | $ZnSO_4/ZnCl_2$ | $(CH_3)_3N \cdot HCl$ | >250 | 23.17 | 3.82 | 10.78 | 42.08 | 20.1/— | — |
| 61 | $ZnCl_2/FeCl_3$ | $(CH_3)_3N \cdot HCl$ | 130 (dec) | 22.71 | 3.78 | 10.31 | 42.55 | 16.1/0.86 | 2.88 |
| 62 | $MnSO_4/CuSO_4$ | $(CH_3)_3N \cdot HCl$ | >250 | 19.78 | 3.64 | 9.24 | 35.35 | 12.8/3.4 | 13.4 |

In Table IV the metal salt complexes are given which are formed by following the procedures of Examples 23, 50, 51, 52, 53, 54, 55, 58, 75, 85, 86 and 87 and utilizing the following molar ratios of reagents:
(a) one mole of a disodium alkylene or phenylene-bis-dithiocarbamate of the formula $R'—C(S)SNa]_2$
(b) two moles of a sodium disubstituted dithiocarbamate of the formula $R'' C(S)SNa$
(c) two moles of a metal salt and,
(d) four moles of either dimethylamine hydrochloride or trimethylamine hydrochloride *

Table V gives the metal salt complexes formed by following the procedures of Examples 23, 50, 51, 52, 53, 54, 55, 58, 75, 85, 86 and 87 when the following molar ratios are utilized:
(a) one mole of disodium ethylene-bis-dithiocarbamate;
(b) two moles of sodium dimethyl dithiocarbamate;
(c) two moles of zinc chloride and;
(d) four moles of amine as the free base.

Table V

| Example No. | $R^1R^2R^3N$ | mp° C | C | H | N | S | Metal | O |
|---|---|---|---|---|---|---|---|---|
| 82 | $(HOCH_2CH_2)_3N$ | 144–50 | 22.45 | 3.82 | 9.75 | 39.59 | 20.6 | 3.32 |
| 83 | $(CH_3CH_2)_2NH$ | 200–8 | 19.82 | 3.39 | 8.21 | 35.83 | 25.9 | 5.70 |
| 84 | $CH_3NH_2$ | 133–6 | 20.11 | 3.34 | 10.15 | 39.47 | 22.9 | 3.68 |
| 85 | $(CH_3)_2NCH_2CH_2OH$ | 211–4 | 20.30 | 3.57 | 8.51 | 34.30 | 24.7 | 5.22 |

Table VI gives the metal salt complexes formed by following the procedure of Example 87 and utilizing the indicated molar ratios.

Table IV

| Example No. | Metal Salt | R | R" | mp° C. | C | H | N | S | Metal | O |
|---|---|---|---|---|---|---|---|---|---|---|
| 64 | $MnSO_4$ | $—NH(CH_2)_6NH—$ | (N-piperidinyl) | 155 (dec) | 36.59 | 4.86 | 10.41 | 30.71 | 9.7 | 6.93 |
| 65 | $MnSO_4$ | $—NH(CH_2)_6NH—$ | $(CH_3)_2N—$ | 170 (dec) | 24.46 | 4.05 | 8.69 | 34.23 | 13.0 | 8.87 |
| 66 | $MnSO_4$ | $—NH(CH_2)_6NH—$ | $CH_3NH—$ | 180 (dec) | 26.21 | 3.65 | 9.06 | 43.64 | 26.9 | 14.74 |
| 67 | $MnSO_4$ | $—NHCH_2CH(CH_3)NH—$ | $(CH_3)_2N—$ | >250 | 20.88 | 3.51 | 9.21 | 35.95 | 19.8 | 9.33 |
| 68 | $MnSO_4$ | $—NH(CH_2)_2NH—$ | $(CH_3)_2N—$ | >250 | 20.28 | 3.41 | 8.62 | 36.11 | 20.7 | 8.01 |
| 69 | $MnSO_4$ | $—NH(CH_2)_2NH—$ | $CH_3NH—$ | 235 (dec) | 17.78 | 3.44 | 10.60 | 36.42 | 12.0 | 16.03 |
| 70 | $MnSO_4$ | $—NH(CH_2)_3NH—$ | $CH_3NH—$ | 250 (dec) | 20.14 | 3.28 | 9.90 | 38.26 | 15.0 | 11.22 |
| 71 | $MnSO_4$ | $—NH(CH_2)_3NH—$ | $PhCH_2NH$ | 215 | 35.56 | 3.85 | 9.83 | 29.32 | 10.5 | 8.32 |
| 72 | $MnSO_4$ | $—NH(CH_2)_4NH—$ | $CH_3NH—$ | 250 | 20.85 | 3.25 | 9.43 | 35.24 | 16.1 | 11.95 |
| 73 | $MnSO_4$ | $—NH(CH_2)_4NH—$ | $(CH_3)_2N$ | 250 | 23.54 | 3.89 | 10.66 | 36.24 | 13.4 | 7.88 |
| 74 | $MnSO_4$ | $—NH(CH_2)_4NH—$ | $CH_3(CH_2)_{11}NH—$ | 120 | 48.66 | 8.11 | 5.75 | 12.22 | 18.4 | 7.87 |
| 75 | $MnSO_4$ | (piperazinyl) | $CH(CH_2)_{11}NH—$ | 200 (dec) | 44.29 | 6.89 | 7.42 | 18.57 | 13.1 | 7.36 |
| 76 | $MnSO_4$ | (phenylene-NH,NH) | $CH_3(CH_2)_{11}NH—$ | 230 (dec) | 48.99 | 6.88 | 8.00 | 23.18 | 8.3 | 5.95 |
| 77 | $MnSO_4$ | $—NH(CH_2)_3NH—$ | $NH_2—$ | 220 (dec) | 22.18 | 3.21 | 11.24 | 34.17 | 15.3 | 11.83 |
| 78* | $FeCl_3$ | $—NH(CH_2)_2NH—$ | $CH_3NH—$ | >250 | 13.35 | 2.14 | 7.49 | 44.74 | 19.6 | 10.97 |
| 79* | $ZnCl_2$ | $—NH(CH_2)_2NH—$ | $CH_3NH—$ | 108–12 | 20.76 | 3.93 | 11.45 | 46.99 | 20.3 | 1.98 |
| 80* | $MnSO_4$ | $—NH(CH_2)_2NH—$ | $CH_3NH—$ | >250 | 15.31 | 2.59 | 9.28 | 36.70 | 19.4 | 17.6 |
| 81* | $CuSO_4$ | $—NH(CH_2)_2NH—$ | $CH_3NH—$ | >250 | 17.09 | 2.89 | 9.26 | 37.66 | 25.5 | — |

Table V gives the metal salt complexes formed by following the procedures of Examples 23, 50, 51, 52, 53, Table VI

| Ex. No. | Zinc Chloride (moles) | HOCH$_2$CH$_2$N$^+$ (CH$_3$)$_3$Cl$^-$ (moles) | EBDC (moles) | DMDC (moles) | mp° C |
|---|---|---|---|---|---|
| 88 | (1.0) | (0.1) | (1.0) | (0.1) | 144 (dec) |
| 89 | (0.75) | (0.5) | (1.0) | (0.1) | 134–6 |
| 90 | (1.2) | (2.0) | (1.0) | (1.0) | 124–6 |
| 91 | (6.0) | (3.0) | (1.0) | (10.0) | 170 (dec) |
| 92 | (1.6) | (0.85) | (1.0) | (2.0) | 175–80 |

The mixed dithiocarbamic acid metal salts of this invention exhibit broad spectrum fungicidal activity when used as a topical fungicide and is especially effective for the foliar control of tomato late blight (*Phytophtora infestans*) on tomato seedlings, grape downy mildew (*Plasmopora viticola*) on grape seedlings, wheat stem rust (*Puccinia graminis* f. sp. tritici) on wheat plants, rice blast (*Piricularia oryzae*) on rice plants and barley net blotch (*Helminthosporium teres*) on barley plants.

In particular the salts of this invention show control of *Botrytis cinerea* on broad beans (*Vicia faba*). This is particularly important since (mancozeb) the zinc complex of maganese ethylene-bis-dithiocarbamate shows no activity against *Botrytis cinerea.*

The salts of this invention exhibit an unexpected activity against *Botrytis cinerea* on broad beans (*Vicia faba*), an activity which is non-existent with ethylene-bis-dithiocarbamates. In this test broad beans are trimmed to a height of approximately 4.5 inches 24 hours prior to chemical application, the plants are sprayed to runoff with the chemical agent and allowed to dry. The plants are inoculated with *Botrytis cinerea* and incubated in a humid environment at 75°-80° F for 66 hours. The plants lesions are evaluated 66 to 68 hours after inoculation.

The control of bean powdery mildew (*Erysiphe polygoni*) is demonstrated by the following procedure. Bean plants (var. Dwarf Hort) are thinned to two plants per pot 24 hours prior to chemical application. The plants are sprayed to runoff with the chemical agent and allowed to dry. The plants are then inoculated with *Erysiphe polygoni* and maintained under existing greenhouse conditions. Treatment comparisions are made 8 to 10 days after inoculation.

The salts of this invention are effective in controlling tomato late blight (*Phytophtora infestans*) on tomato seedlings. In this test, the plants are sprayed to runoff with suspensions of agents under evaluation in the given dosage series. The sprayed plants are allowed to dry and are then inoculated with a suspension of the *Phytophthora infestans* fungal spores. The plants are maintained at a 60° to 62° F. temperature and 100% relative humidity for about 40 hours to incubate the spores. The plants are then stored in light at 75° F. for 5 to 6 days at which time disease control estimates are made.

Data for the foliar control of rice blast (Piricularia oryzae) on rice plants is demonstrated as follows: Rice plants are trimmed to a height of approximately 5 inches 24 hours prior to chemical application. The plants are sprayed to runoff with the chemical agent, allowed to dry and then inoculated with *Piricularia oryzae* and maintained in a humid environment (75°-85° F) for 24 hours. The plants are then maintained in a greenhouse environment for 7-8 days after inoculation at which time disease control estimates are made.

The foliar control of grape downy mildew (*Plasmopora viticola*) on grape seedlings is demonstrated by the following test. The grape seedlings are sprayed to runoff with suspensions of agents under evaluation in the given dosage series. The sprayed plants are allowed to dry and are then inoculated with a suspension of the *Plasmopora viticola* fungal spores. The inoculated plants are incubated in a humid environment at 65°-70° F for 48 hours then stored in light at 75° F for 7 days. The plants are then evaluated for fungal growth.

The salts of this invention are effective against barley net blotch (*Helminthosporium teres*) on barley plants. In this test barley plants are trimmed to a height of approximately 2.5 inches 24 hours prior to chemical application. The plants are sprayed to runoff with the chemical agent and allowed to dry. The plants are then inoculated with *Helminthosporium teres* and incubated in a humid environment at 75°-80° F for 24 hours. The plants are then transferred to a greenhouse (70°-75° F) for 6 to 7 days at which time they are evaluated by counting the lesions.

The control of wheat stem rust (*Puccinia graminis*) is demonstrated by the following procedure. Seven-day-old wheat plants (var. Monon) are trimmed to approximately 2.5 inches 24 hours prior to chemical application to provide a uniform plant height and to facilitate uniform inoculation. The plants are sprayed to runoff with the chemical agent, allowed to dry and then are inoculated with *Puccinia graminis.* The plants are maintained in a humid environment at about 68° F. and are never allowed to exceed 85° F. A timer is used to permit 12 hours of continuous darkness followed by a minimum of 3 to 4 hours of light with an intensity of 500 ft. candles. At the end of the light period the fogger is turned off and the plants are allowed to dry prior to being placed in a greenhouse environment where they are grown for 2 weeks at which time treatment comparisons are made.

The results of these biological test are given below in Table VII. In this table salts which exhibited a 70% or greater control of a particular fungus are indicated by a + sign and those which exhibited less than 70% control are indicated by a − sign. In this table the results of the test against the following fungi were presented:

BOT — broad bean gray mold leaf spot (*Botrytis cinerea*)
BPM — bean powdery mildew (*Erysiphe polygoni*)
TLB — tomato late blight (*Phytophtora infestans*)
RB — rice blast (*Piricularia oryzae*)
GDM — grape downy mildew (*Plasmopora viticola*)
BH — barley net blotch (*Helminthosporium teres*)
WSR — wheat stem rust (*Puccinia graminis*)

TABLE VII

| Example No. | Disease Control Level at 150 ppm | | | | | | |
|---|---|---|---|---|---|---|---|
| | BOT | BPM | TLB | RB | GDM | BH | WSR |
| 1 | − | + | + | | + | − | |
| 2 | + | + | + | + | + | + | |
| 3 | + | − | + | + | + | − | + |
| 4 | + | − | + | + | + | − | + |
| 5 | + | − | + | + | + | − | + |
| 6 | + | − | + | + | + | − | + |
| 7 | + | − | + | + | + | + | + |
| 8 | + | − | − | + | + | − | + |
| 9 | + | − | − | + | + | − | + |
| 10 | + | − | + | + | + | − | + |
| 11 | + | − | + | + | + | − | + |
| 12 | + | − | − | + | + | − | + |
| 13 | + | − | + | + | + | − | |
| 14 | + | − | + | + | + | − | + |
| 15 | + | − | − | + | + | − | + |
| 16 | − | − | − | + | + | − | + |
| 17 | + | − | − | + | + | − | − |
| 18 | + | − | + | + | + | − | + |
| 19 | + | + | − | + | + | + | + |
| 20 | + | − | − | + | + | − | + |
| 21 | + | − | − | − | + | − | + |

TABLE VII-continued

| Example No. | Disease Control Level at 150 ppm | | | | | | |
|---|---|---|---|---|---|---|---|
| | BOT | BPM | TLB | RB | GDM | BH | WSR |
| 22 | + | − | − | − | + | − | − |
| 23 | + | − | − | − | + | − | − |
| 24 | + | − | − | − | + | − | − |
| 25 | + | − | − | + | + | + | + |
| 26 | + | − | − | + | + | − | + |
| 27 | + | − | − | − | + | + | − |
| 28 | + | − | − | + | + | + | − |
| 29 | + | + | − | − | + | + | − |
| 30 | + | + | − | + | + | − | − |
| 31 | + | − | − | + | + | − | − |
| 32 | + | − | − | − | + | − | − |
| 33 | + | + | − | − | + | + | + |
| 34 | + | − | − | + | + | − | + |
| 35 | + | − | − | + | + | − | + |
| 36 | + | + | − | + | + | − | + |
| 37 | + | − | − | + | − | − | − |
| 38 | − | − | − | + | − | − | + |
| 39 | + | − | − | − | + | − | + |
| 40 | + | − | − | + | + | − | − |
| 41 | − | − | − | + | + | − | + |
| 42 | + | − | − | + | + | − | − |
| 43 | − | − | − | + | + | − | − |
| 44 | − | − | − | − | + | − | + |
| 45 | − | − | − | + | + | − | − |
| 46 | + | − | − | + | + | − | − |
| 47 | + | − | − | + | − | − | − |
| 48 | + | − | − | + | + | − | − |
| 49 | + | − | − | + | + | − | + |
| 50 | + | + | + | + | + | + | − |
| 51 | + | − | + | + | + | + | − |
| 52 | + | + | + | + | + | − | − |
| 53 | + | − | + | | + | + | + |
| 54 | + | − | + | | + | + | − |
| 55 | + | + | + | + | + | + | − |
| 56 | − | − | − | + | − | − | − |
| 57 | + | − | − | − | + | − | − |
| 58 | + | − | − | + | + | + | + |
| 59 | + | − | − | + | − | − | − |
| 60 | + | + | + | + | + | − | − |
| 61 | − | − | + | + | + | − | + |
| 62 | + | − | − | + | + | − | − |
| 64 | − | − | − | + | − | − | − |
| 65 | + | − | − | + | − | − | − |
| 66 | − | − | − | + | − | − | − |
| 67 | + | − | − | + | + | − | + |
| 68 | + | + | − | + | + | − | + |
| 69 | − | − | − | + | − | − | − |
| 70 | − | + | − | + | − | − | − |
| 71 | − | + | − | + | − | − | − |
| 72 | − | − | − | + | − | − | − |
| 73 | + | − | − | + | − | − | − |
| 74 | − | − | − | + | − | − | − |
| 75 | − | − | − | + | − | − | − |
| 76 | − | − | − | + | − | − | − |
| 77 | − | − | − | + | − | − | + |
| 78 | − | + | − | + | − | − | − |
| 79 | − | − | + | + | + | − | + |
| 80 | − | − | − | + | − | − | − |
| 81 | − | − | − | + | − | − | − |
| 82 | + | − | − | + | + | − | + |
| 83 | + | + | − | + | + | − | + |
| 84 | + | − | + | + | + | + | + |
| 85 | + | − | + | + | + | − | − |
| *86 | + | + | + | + | + | − | + |

*at 300 ppm

The metal salts of mixed dithiocarbamic acids of this invention are useful as agricultural fungicides and as such may be applied to various loci such as the seed, the soil or the foliage. For such purposes these metal salts may be used in the technical or pure form as prepared, as solutions or as formulations. The metal salts are usually taken up in a carrier or are formulated so as to render them suitable for subsequent dissemination as fungicides. For example, these metal salts may be formulated as wettable powders, emulsifiable concentrates, dusts, granular formulations, aerosols, or flowable emulsion concentrates. In such formulations, the salts are extended with a liquid or solid carrier and, when desired suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art may be found in the John W. McCutcheon, Inc. publication "Detergents and Emulsifier, Annual."

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of 20% to 98%, preferably 40% to 75%. A typical wettable powder is made by blending 50 parts of tetramethylammonium zinc ethylene-bis-dithiocarbamic acid-dimethyldithiocarbamic acid, 45 parts of a synthetic precipitated hydrated silicon dioxide sold under the trademark Hi-Sil ®, and 5 parts of sodium lignosulfonate (Marasperse ® N-22). In another preparation a kaolin type (Barden) clay is used in place of the Hi-Sil in the above wettable powder, and in another such preparation 25% of the Hi-Sil is replaced with a synthetic sodium silico aluminate sold under the trademark Zeolex ® 7.

Dusts are prepared by mixing the metal salt with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing 20% to 80% of the active ingredient are commonly made and are subsequently diluted to 1% to 10% use concentration.

The metal salts can be applied as fungicidal sprays by methods commonly employed, such as conventional high gallonage hydraulic sprays, low gallonage sprays, airblast spray, aerial sprays and dusts. The dilution and rate of application will depend upon the type of equipment employed, the method of application and diseases to be controlled, but the effective amount is usually 0.1 lb. to 25 lbs. per acre of the active ingredient.

As a seed protectant, the amount of toxicant coated on the seed is usually at a dosage rate of about 0.1 to 20 ounces per hundred pounds or seed. As a soil fungicide the chemical may be incorporated in the soil or applied to the surface usually at a rate of 0.1 to 25 lbs. per acre. As a foliar fungicide, the toxicant is usually applied to growing plants at a rate of 0.25 to 10 pounds per acre.

Fungicides which may be combined with the fungicides of this invention include:

(a) Nitrophenol derivatives such as:
dinitro-(1-methylheptyl)phenyl crotonate (dinocap), 2-sec-butyl-4,6-dinitrophenyl 3,3-dimethyl acrylate (binapacryl), and 2-sec-butyl-4,6-dinitrophenyl isopropyl carbonate;

(b) heterocyclic structures such as:
N-trichloromethylthiotetrahydro-phthalimide (captan), N-trichloromethylthiophthalimide (folpet), 2-heptadecyl-2-imidazoline acetate (glyodin) 2-octylisothiazolone-3, 2,4-dichloro-6-(o-chloroanilino)-s-triazine, diethyl phthalimido-phosphorothioate, 4-butyl-1,2,4-triazole, 5-amino-1-[bis(dimethylamino)phosphinyl]-3-phenyl-1,2,4-triazole, 5-ethoxy-3-trichloromethyl-1,2,4-thiadizole, 2,3-dicyano-1,4-dithiaanthraquinone (dithianon), 2-thio-1,3-dithio-[4,5-b]quinoxaline (thioquinox). methyl 1-(butylcarbamoyl)-2-benzimidazole carbamate (benomyl), 2-(4-thiazolyl)benzimidazole, 4-(2-chlorophenylhydrazono)-3-methyl-5-isoxazolone, pyridine-2-thiol-1-oxide, 8-hydroxyquinoline sulfate. 2,3-dihydro-5-carboxanilido-6-methyl-1,4-oxathiin-4,4-dioxide, 2,3-dihydro-5-carboxanilido-6-methyl-1,4-oxathiin-4,4-dioxide, 2,3-dihydro-5-carboxanilido-6-methyl-1,4-oxathiin, α-(phenyl)-α-(2,4-dichlorophenyl)-5-pyrimidinylmethanol (triarimol), cis-N-[(1,1,2,2-tetrachloroethyl)thio]-4-cyclohexene-1,2-dicarboximide, 3[2-(3,5-dimethyl-2-oxycyclohexyl-2-hydroxy]glutarimide (cycloheximide), and dehydroacetic acid;

(c) Miscellaneous halogenated fungicides such as:
tetrachloro-p-benzoquinone (chloranil), 1,4-dichloro-2,5-dimethoxybenzene(chloroneb), 2,3-dichloro-1,4-naphthoquinone (dichlone), 3,5,6-trichloro-o-anisic acid (tricamba), 2,4,5,6-tetrachloroisophthalonitrile, 2,6-dichloro-4-nitroaniline (DCNA), 2-chloro-1-nitropropane, polychloronitrobenzenes such as: pentachloronitrobenzene (PCNB) and tetrafluorodichloroacetone;

(d) Fungicidal antibiotics such as:
griseofulvin, kasugamycin and streptomycin;

(e) Copper-based fungicides such as:
cuprous oxide, basic cupric chloride, basic copper carbonate, copper naphthenate, and bordeaux mixture; and (f) Miscellaneous fungicides such as:
diphenyl, dodecylguanidine acetate (dodine), phenylmercuic acetate, N-ethylmercuri-1,2,3,6-tetrahydro-3,6-endomethano-3,4,5,6,7,7-hexachlorophthalimide, phenylmercuric monoethanolammonium lactate, p-dimethylaminobenzenediazo sodium sulfonate, methyl isothiocyanate, 1-thiocyano-2,4-dinitrobenzene, 1-phenylthiosemicarbazide, nickel-containing compounds, calcium cyanamide, lime sulfur, sulfur, and 1,2-bis(3-methoxycarbonyl-2-thioureido(-benzene (thiophanatemethyl)

The complex metal salts of mixed dithiocarbamic acids of this invention can be advantageously employed in various ways. Since these complexes possess broad spectrum fungicidal activity they can be employed in the storage of cereal grain. These complexes can also be employed as fungicides in turf and orchard applications. Other applications of the complexes of this invention such as use on various food crops and their habitat will suggest themselves to those skilled in the art of agriculture and horticulture.

We claim:

1. A metal salt of the formula:

$$[M]_a[Y]_b[A(NHC(=S)-S)_2]_x[(R)_2NC(=S)-S]_y \cdot XO_2$$

wherein M is a metal cation selected from groups IIA, IIIA, IVA,
IB, IIB, VIB, VIIB and VIII of the Periodic Table; Y is the group

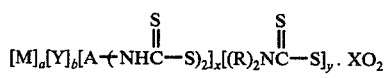

where $R^1$, $R^2$, $R^3$ and $R^4$ are independently hydrogen; ($C_1$-$C_{20}$) unsubstituted alkyl; unsubstituted phenyl naphthyl, benzyl or phenethyl; phenyl, naphthyl, benzyl or phenethyl substituted with up to three substituents selected from the group consisting of methyl, ethyl, methoxy, ethoxy, fluoro, chloro, bromo, iodo, nitro or trihalomethyl; ($C_1$-$C_{20}$) hydroxyalkyl; or ($C_1$-$C_{20}$) haloalkyl; $a$, $b$, $x$ and $y$ are integers; $2a + b = 2x + y$;

A is a phenylene or an alkylene chain of 2 to 6 carbon atoms which may be branched or straight chained;
and R is hydrogen or ($C_1$-$C_4$) alkyl.

2. A metal salt according to claim 1 wherein M is a metal cation selected from the group consisting of Mg, Ca, Ba, Al, Pb, Cu, Zn, Cd, Cr, Mn, Fe, Co and Ni or combinations thereof.

3. A metal salt according to claim 2 wherein A is an alkylene chain of 2 to 6 carbon atoms.

4. A method for controlling phytopathogenic fungi which comprises applying a fungicidally effective amount of a salt according to claim 1 to a plant, to plant seeds or to the plant habitat.

5. A method according to claim 4 wherein the salt is applied to the plant, the plant seeds or the plant habitat at a rate of 0.1 to 25 lbs. per acre.

6. A fungicidal composition which comprises an agronomically acceptable carrier and as the active ingredient, a salt as set forth in claim 1.

7. A process for the preparation of a fungicide which comprises:
mixing aqueous or alcoholic solutions of an alkali metal salt of one mole of an alkylene-bis-dithiocarbamate of the formula:

 (I)

wherein A is phenylene or ($C_2$-$C_6$) alkylene; about 0.1 to 10 moles of an alkali metal salt of an alkyl or dialkyl-dithiocarbamate of the formula:

 (II)

wherein R is independently selected from the group consisting of hydrogen and ($C_1$-$C_4$) alkyl; about 0.1 to 6.0 moles of an ammonium or phosphonium salt the cation of which has the formula:

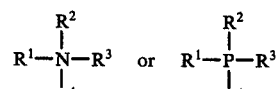

(IV)  (V)

wherein $R^1$, $R^2$, $R^3$ and $R^4$ are independently hydrogen; ($C_1$-$C_{20}$) unsubstituted alkyl; unsubstituted phenyl, naphthyl, benzyl or phenethyl; phenyl, naphthyl, benzyl or phenethyl substituted with up to three substituents selected from the group consisting of methyl, ethyl, methoxy, ethoxy, fluoro, chloro, bromo, iodo, nitro or trihalomethyl; ($C_1$-$C_{20}$) hydroxyalkyl; or ($C_1$-$C_{20}$) haloalkyl; then adding to this mixture an aqueous or alcoholic solution of about 0.75 to about 6.0 moles of a polyvalent metal salt.

8. A process according to claim 7 wherein the reaction is carried out at temperatures from about 20° C. to about 80° C.

9. A process according to claim 8 wherein the resultant precipitate is filtered and dried at about 40° C. to a constant weight.

10. A process according to claim 9 wherein a solution of compounds of Formula (I) and a solution of compounds of Formula (II) are added simultaneously with a solution of polyvalent metal salt to a solution of a group of Formula (IV or (V).

11. A process according to claim 10 wherein A is ($C_2$-$C_6$) alkylene and $R^1$, $R^2$, $R^3$ and $R^4$ are independently hydrogen, ($C_1$-$C_{10}$) unsubstituted alkyl, ($C_1$-$C_{10}$) hydroxyalkyl, or unsubstituted phenyl, benzyl or phenethyl.

12. A process according to claim 10 wherein 1.0 mole of the sodium salt of ethylene-bis-dithiocarbamate; about 2 moles sodium of dimethyldithiocarbamate; about 4 moles of trimethyl (2-hydroxyethyl) ammonium chloride and about 2 moles of zinc chloride are reacted at temperatures from about 25° C. to about 40° C. in an aqueous solvent.

13. A metal salt of the formula:

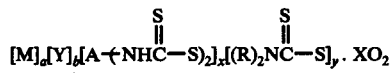

wherein M is a metal cation selected from the group consisting of Mg, Ca, Ba, Al, Pb, Cu, Zn, Cd, Cr, Mn, Fe, Co, and Ni, or combinations thereof; Y is the group

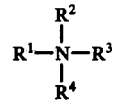

wherein $R^1$, $R^2$, $R^3$, and $R^4$ are independently selected from the group consisting of hydrogen, ($C_1$-$C_{10}$) unsubstituted alkyl, ($C_1$-$C_{10}$) hydroxyalkyl, and unsubstituted phenyl, benzyl or phenethyl; $a$, $b$, $x$ and $y$ are integers; $2a + b = 2x + y$; A is an alkylene chain of 2 to 6 carbon atoms; and R is hydrogen or ($C_1$-$C_4$) alkyl.

* * * * *